(12) United States Patent
Scott et al.

(10) Patent No.: US 7,491,389 B2
(45) Date of Patent: Feb. 17, 2009

(54) MODULATING ANGIOGENESIS

(75) Inventors: Edward W. Scott, Gainesville, FL (US);
Maria Grant, Archer, FL (US); W. Stratford May, Gainesville, FL (US)

(73) Assignee: University of Florida Reasearch Foundation, Inc., Gainsville, FL (US)

( * ) Notice: Subject to any disclaimer, the term of this patent is extended or adjusted under 35 U.S.C. 154(b) by 388 days.

(21) Appl. No.: 10/392,439

(22) Filed: Mar. 18, 2003

(65) Prior Publication Data

US 2003/0180265 A1 Sep. 25, 2003

Related U.S. Application Data

(60) Provisional application No. 60/367,078, filed on Mar. 21, 2002, provisional application No. 60/429,744, filed on Nov. 27, 2002, provisional application No. 60/448,691, filed on Feb. 19, 2003.

(51) Int. Cl.
*A61K 39/395* (2006.01)
*A61K 39/00* (2006.01)

(52) U.S. Cl. ............... 424/130.1; 424/141.1; 424/145.1

(58) Field of Classification Search .............. 530/387.1; 424/130.1, 93.1, 93.7
See application file for complete search history.

(56) References Cited

U.S. PATENT DOCUMENTS

| 5,837,680 | A | | 11/1998 | Moses et al. |
| 5,851,999 | A | * | 12/1998 | Ullrich et al. ................. 514/44 |
| 6,248,327 | B1 | | 6/2001 | Daniel et al. |
| 2001/0008961 | A1 | * | 7/2001 | Hecker et al. ............... 604/117 |
| 2004/0209837 | A1 | * | 10/2004 | Kishimoto et al. ............ 514/44 |

FOREIGN PATENT DOCUMENTS

WO WO 99/50461 10/1999
WO WO 01/94420 12/2001

OTHER PUBLICATIONS

Aiello et al. Suppression of retinal neovascularization in vivo by inhibition of vascular endothelial grouwht factor using soluble VEGF-receptor chimeric protein. PNAS. 1995;92:10457-10461.*
Antoszyk et al. The effects of intravitreal triamcinolone acetonide on experimental pre-retinal neovascularization. Graefe's Arch Clin Exp Opthalmol. 1993, 231:34-40.*
Grant et al. The role of growth factors in pathogenesis of diabetic retinopathy. Exper Opin. Investig. Drugs. 2004;13(10):1275-1293.*
Sengupta et al. Preventing stem cell incorporation into choroidal neovascularization by targeting homing and attachment factors. Investigative Opthalmology&Visual Science. 2005;46(1):343-348.*
Chung et al. Lineage analysis of the hemangioblast as defined by Flk1 and SCL expression. Development, 2002, 129:5511-5520.*
Imai et al. Blood. 1999. 93;1:149-156.*
The Merck Manual of Diagnosis and Therapy, 17th edition, 1999, published by Merck Research Laboratories, pp. 729-730.*
The American Heritage Dictionary (2nd College Edition, 1982, published by Houghton Mifflin Company. p. 933.*
Kocher et al., Neovascularization of ischemic myocardium by human bone-marrow-derived angioblasts prevents cardiomyocyte apoptosis, reduces remodeling and improves cardiac function, Nature Medicine, 7(4): 430-436 (Apr. 2001).
Adamis et al., Inhibition of Vascular endothelial Growth Factor Prevents Retinal Ischemia-Associated Iris Neovascularization in a Non-human Primate, 114:66-71 (1996).
J. M. Butler et al, "SDF-1 is Both Necessary and Sufficient to Promote Proliferative Retinopathy", The Journal of Clinical Investigation, vol. 115 No. 1, 2005, pp. 86-93.

* cited by examiner

*Primary Examiner*—Maher M Haddad
*Assistant Examiner*—Chun Dahle
(74) *Attorney, Agent, or Firm*—Akerman Senterfitt; Gregory A. Nelson; Amy A. Dobbelaere

(57) ABSTRACT

Hemangioblasts in adult bone marrow participate in new blood vessel formation. By modulating the differentiation of hemangioblasts into blood vessel cells, angiogenesis in a particular tissue can be increased or decreased. Intravitreal injection of antibodies that block SDF-1 activity inhibited induced retinal neovascularization mediated by hemangioblasts.

6 Claims, No Drawings

MODULATING ANGIOGENESIS

CROSS REFERENCE TO RELATED APPLICATION

This application claims the priority of U.S. provisional patent application Ser. No. 60/367,078, filed Mar. 21, 2002; U.S. provisional patent application Ser. No. 60/429,744 filed Nov. 27, 2002; and U.S. provisional patent application Ser. No. 60/448,691 filed Feb. 19, 2003.

STATEMENT AS TO FEDERALLY SPONSORED RESEARCH

The invention was made with United States government support under grant numbers HL70738, EY012601, EY007739, CA72769, and DK52558 awarded by the National Institutes of Health. The United States government has certain rights in the invention.

FIELD OF THE INVENTION

The invention relates to the fields of medicine, angiogenesis, and stem cell biology. More particularly, the invention relates to compositions and methods for modulating angiogenesis.

BACKGROUND

Adult bone marrow (BM)-derived hematopoietic stem cells (HSC) are defined by their ability to self renew while functionally repopulating the cells of the blood and lymph for the life of an individual. See, Müller-Sieburg, C. (ed.) Hematopoietic stem cells: animal models and human transplantation (Springer-Verlag, New York, 1992). These abilities make HSC clinically useful in therapeutic BM transplantation for a variety of BM failure states including the hematological malignancies leukemia and lymphoma. HSC can be highly enriched and quantified by known methods. See, e.g., Harrison et al. Exp Hematol 21, 206-19 (1993). Like other tissue-derived stem cells, HSC are thought to retain a high capacity for "plasticity" that would allow for the potential contribution of regenerative progenitors to non-hematopoietic tissues following injury or stress. Goodell et al., Ann NY Acad Sci. 938, 208-18; discussion 218-20 (2001); Krause et al., Cell 105, 369-77 (2001).

Indeed, following full and durable reconstitution of a lethally irradiated mouse with a single BM-derived HSC, donor cells were identified in multiple tissues such as the brain, heart, skeletal muscle, liver, and endothelial cells. Krause et al., supra. Although the experimental design of that study yielded low levels (<5%) of donor contribution to non-hematopoietic tissues, the results suggest the possibility of functional regeneration of multiple tissues by HSC-derived progenitors. In other transplant models hematopoietic progenitors have been shown to repopulate hepatocytes in the parenchymal liver to restore liver function following chemically induced injury (Petersen et al., Science 284, 1168-70. (1999); Lagasse et al., Nat Med 6, 1229-34 (2000)), and to regenerate myocardium to improve cardiac function following infarction (Orlic et al., Nature 410, 701-5 (2001)).

Diabetic retinopathy and retinopathy of prematurity are among the leading causes of vision impairment throughout the world. Retinal neovascularization is thought to occur in response to an hypoxic insult which leads to changes in the existing vasculature and compensatory, albeit pathologic, new capillary growth. Grant et al., Diabetes 35, 416-20 (1986); Limb et al., Br J Ophthalmol 80, 168-73 (1996). Postnatal neovascularization has been attributed to angiogenesis, a process characterized by sprouting of new capillaries from pre-existing blood vessels. Folkman and Shing, J Biol Chem 267, 10931-4 (1992). Several studies have shown that endothelial progenitor cells (EPC) capable of contributing to in vitro capillary formation can be derived from BM cells. Asahara et al., Science 275, 964-7 (1997); Gehling et al., Blood 95, 3106-12 (2000); Bhattacharya et al., Blood 95, 581-5 (2000); Lin et al., J Clin Invest 105, 71-7 (2000). Pro-angiogenic growth factors such as vascular endothelial growth factor (VEGF, See, e.g., Asahara et al., Embo J 18, 3964-72 (1999); Kalka et al., Circ. Res. 86, 1198-202 (2000)), and granulocyte/macrophage colony stimulating factor (GM-CSF) (see, e.g., Takahashi et al., Nat Med 5, 434-8 (1999)) increase circulating levels of EPC in the adult and promote new blood vessel formation. Recently, it was demonstrated that hydroxymethylglutaryl (HMG)-CoA reductase inhibitors potently augment EPC differentiation by a mechanism involving the angiogenic protein kinase Akt. Dimmeler, et al., J Clin Invest 108, 391-7 (2001). Studies also support the contribution by EPC to blood vessel formation in the adult (Asahara et al., Embo J 18, 3964-72 (1999); Kalka et al., supra; Crosby et al., Circ Res 87, 728-30 (2000); Murohara et al., J Clin Invest 105, 1527-36 (2000)), and in cardiac reperfusion post ischemia (Kocher et al., Nat Med 7, 430-6 (2001); Kawamoto et al., Circulation 103, 634-7 (2001)). However, as these studies were based on short-term transplant and acute injury models, it is not clear whether the cell giving rise to EPCs is the long-term repopulating HSC or other progenitors such as the mesenchymal stem cell.

Within the developing embryo, pluripotent progenitors are generated that are capable of contributing to the formation of blood and blood vessels, a process called hemangiogenesis. Choi, K., Biochem Cell Biol 76, 947-56 (1998); Takakura, et al., Cell 102, 199-209 (2000). These pluripotent stem cells are termed hemangioblasts. Hemangioblasts can also be produced from embryonic stem cells during in vitro differentiation in response to vascular endothelial growth factor. Choi, supra. Heretofore, however, definitive evidence for the existence of the hemangioblast within the adult BM, and in particular for a functional role of such BM-derived cells in new blood vessel formation was lacking.

SUMMARY

The invention relates to the discovery that hemangioblasts can be isolated from adult BM. Isolated hemangioblasts can clonally differentiate into all hematopoietic cell lineages as well as blood and blood vessel cells that revascularize adult retina. Because of their ability to promote neovascularization, adult hemangioblasts contribute to ischemia-induced retinal vascular diseases such as diabetic retinopathy and retinopathy of prematurity. Such cells thus represent a new therapeutic target in the treatment of the diseases associated with angiogenesis. For example, compositions and methods of the invention may be useful for treating and preventing cancerous tumor growth by restricting blood supply. Further due to their ability to promote new vessel growth, the therapeutic potential of hemangioblasts can be applied to any disease where vascular endothelium is defective or has been damaged, e.g., ischemia, such as cardiac ischemia.

The invention also relates to the discovery that hemangioblast-mediated neovascularization can be inhibited by blocking SDF-1 (e.g., SDF-1alpha) activity, e.g., using anti-SDF-1 antibodies. As an example, intravitreal injection of neutralizing anti-SDF-1 antibodies completely blocked hemangioblast-derived neovascularization of ischemic retinas. Modulating SDF-1 activity thus might be used to treat or prevent diabetic retinopathy or other diseases related to aberrant vessel formation.

Accordingly, the invention features a method for modulating angiogenesis in a target tissue in a subject. This method includes a non-naturally occurring step of modulating the level of differentiation of hemangioblasts to blood vessel cells in the subject. In some variations, the step of modulating the level of differentiation of hemangioblasts to blood vessel cells in the subject includes increasing or decreasing the number of hemangioblasts in the subject. Increasing the number of hemangioblasts in the subject can be performed by administering hemangioblasts to the subject. The hemangioblasts administered to the subject may be derived from cells that were removed from the subject. In some variations, the cells that were removed from the subject can be expanded in vitro prior to being administered to the subject. In another variation, hemangioblasts administered to the subject may be derived from cells from a donor other than the subject. The cells from the donor may be expanded in vitro prior to being administered to the subject.

The step of modulating the level of differentiation of hemangioblasts to blood vessel cells in the subject also includes decreasing the number of hemangioblasts in the subject. To decrease the number of hemangioblasts in the subject, an agent that depletes hemangioblasts may be administered to the subject. In one variation of this method, the agent is an antibody that specifically binds a molecule present on the surface of hemangioblasts.

In another embodiment, the step of modulating the level of differentiation of hemangioblasts to blood vessel cells in the subject includes increasing or decreasing the recruitment of hemangioblasts from bone marrow to a non-bone marrow compartment.

In another aspect, the invention features a method for decreasing blood vessel formation in a subject. In one variation, this method includes administering to the subject an agent that blocks the activity of SDF-1. The agent can be an antibody that specifically binds SDF-1. In one variation of this method, the agent is administered to an eye of the subject.

Also featured within the invention is a hemangioblast isolated from adult bone marrow. The adult bone marrow can be mammalian bone marrow.

In yet another aspect, the invention features a method for isolating an hemangioblast from the bone marrow of an adult animal. This method includes isolating bone marrow from the animal, wherein the bone marrow includes a hemangioblast and a non-hemangioblast cell; separating the hemangioblast and the non-hemangioblast cell; and collecting the hemangioblast. The step of separating the hemangioblast and the at least one non-hemangioblast cell can include contacting the bone marrow with an agent that specifically binds the hemangioblast but not the non-hemangioblast cell. In another variation of this method, the step of separating the hemangioblast and the non-hemangioblast cell can include contacting the bone marrow with an agent that specifically binds the non-hemangioblast cell but not the at least one hemangioblast. The agent can be an antibody.

Unless otherwise defined, all technical terms used herein have the same meaning as commonly understood by one of ordinary skill in the art to which this invention belongs.

Use of the term "hemangioblast" refers to a pluripotent stem/progenitor cell capable of long-term self-renewal and clonally contributing to the formation of blood vessels.

By the term "angiogenesis" is meant the process of vascularization of a tissue involving the development of new blood vessels.

Use of the term "neovascularization" means the formation of new blood vessels.

Use of the term "differentiation" means the changes from simple to more complex forms undergone by developing cells so that they become more specialized for a particular function.

As used herein, "adult bone marrow" means bone marrow from a postnatal organism.

Although methods and materials similar or equivalent to those described herein can be used in the practice or testing of the present invention, suitable methods and materials are described below. All publications, patent applications, patents and other references mentioned herein are incorporated by reference in their entirety. In the case of conflict, the present specification, including definitions will control. The particular embodiments discussed below are illustrative only and not intended to be limiting.

DETAILED DESCRIPTION

The invention provides hemangioblasts isolated from BM as well as methods and compositions for modulating angiogenesis in a target tissue in a subject. Compositions include a hemangioblast isolated from adult BM. In one method, angiogenesis in a target tissue is modulated by a non-naturally occurring step of modulating the level of differentiation of hemangioblasts to blood vessel cells in the subject. For example, to encourage angiogenesis in an ischemic tissue (e.g., myocardium), the differentiation of hemangioblasts to blood vessel cells can be increased by increasing the number of hemangioblasts in the subject. As another example, to reduce angiogenesis in a target tissue (e.g., a retina after hypoxic insult), the differentiation of hemangioblasts to blood vessel cells can be decreased or blocked by decreasing the number of hemangioblasts in the subject. For instance, as described below, intravitreal injection of anti-SDF-1 antibodies inhibited retinal angiogenesis. Accordingly, the methods and compositions of the invention might be used to treat a number of disorders associated with aberrant blood vessel formation.

Biological Methods

Methods involving conventional molecular biology techniques are described herein. Such techniques are generally known in the art and are described in detail in methodology treatises such as Molecular Cloning: A Laboratory Manual, 3rd ed., vol. 1-3, ed. Sambrook et al., Cold Spring Harbor Laboratory Press, Cold Spring Harbor, N.Y., 2001; and Current Protocols in Molecular Biology, ed. Ausubel et al., Greene Publishing and Wiley-Interscience, New York, 1992 (with periodic updates). Immunological methods (e.g., preparation of antigen-specific antibodies, immunoprecipitation, and immunoblotting) are described, e.g., in Current Protocols in Immunology, ed. Coligan et al., John Wiley & Sons, New York, 1991; and Methods of Immunological Analysis, ed. Masseyeff et al., John Wiley & Sons, New York, 1992. Conventional methods of gene transfer and gene therapy can also be adapted for use in the present invention. See, e.g., Gene Therapy: Principles and Applications, ed. T. Blackenstein, Springer Verlag, 1999; Gene Therapy Protocols (Methods in Molecular Medicine), ed. P. D. Robbins, Humana Press, 1997; and Retro-vectors for Human Gene Therapy, ed. C. P. Hodgson, Springer Verlag, 1996. Methods of stem cell transplantation are described herein. Such techniques are generally known in the art and are described in detail in Hematopoietic stem cells: animal models and human transplantation, ed. Muller-Sieburg, C., Springer Verlag, NY 1992.

Hemangioblasts Isolated from BM

The invention provides hemangioblasts isolated from adult BM. Hemangioblasts of the invention are HSC that are a source of more differentiated and developmentally restricted progenitors that lack the ability of long-term self-renewal, for example circulating endothelial progenitor cells found in the peripheral blood. The source of the BM from which hemangioblasts are isolated may be from any suitable animal, i.e., any animal having BM containing hemangioblasts. For use in various methods of the invention, the source of BM may be from a non-adult organism, e.g., an embryo. BM can be isolated from an animal using any suitable method. For example, BM may be isolated by needle aspiration of marrow directly from the bone. Hemangioblasts may be isolated from BM using markers differentially expressed on hemangioblasts compared to other BM cells. For example, in human BM, hemangioblasts are positive for marker CD34, and negative for markers CD38 and Lin. Additionally, human hemangioblasts may be isolated using the AC133 marker, or other markers of hematopoietic stem cells. Many different techniques for isolating cells based on marker expression are known, e.g., antibody-based methods, such as immunopanning, magnetic bead separation, and fluorescence activated cell sorting (FACS). As a specific example, BM harvested from a rodent donor is made into a single cell suspension and plated onto tissue culture dishes in IMDM+20% fetal bovine serum (FBS) for 4 hours. Non-adherent cells are collected and several rounds (e.g., three rounds) of lineage antibody depletion (B220, CD3, CD4, CD8, CD11b, Gr-1, TER 119) are performed with a suitable cell sorting system (e.g., Miltyni MACS system) until a small aliquot stained with PE-conjugated lineage antibody cocktail shows greater than approximately 95% lineage-negative by FACS. The Lin– cells are then positively selected for Sca-1 for 2-3 rounds until an aliquot showing greater than approximately 95% Sca-1+, Lin– purity has been achieved. The Sca-1+, Lin– cells are then stained for CD45 to confirm hematopoietic origin. Similar hematopoietic stem cell enrichments are possible for humans to isolate CD34+, CD38–, Lin– cells via either magnetic bead or flow cytometric separation techniques.

Hemangioblasts useful in methods of the invention may include a nucleic acid encoding a detectable label (e.g., green fluorescent protein (GFP)). For example, hemangioblasts containing a nucleic acid encoding GFP are easily visualized by a green fluorescence and are particularly useful in settings where it is desirable to detect the cells as well as daughter cells in newly formed vasculature. Specifically, hemangioblasts may contain a nucleic acid harboring a strong promoter and enhancer (e.g., chicken beta-actin promoter and CMV immediate early enhancer) operably linked to a nucleotide sequence encoding GFP. A description of the gfp+ transgenic mouse strain used as the donor strain in experiments described herein is in Example 1.

Modulating Angiogenesis of a Target Tissue

Also included within the invention is a method of modulating angiogenesis of a target tissue in a subject. The method includes a non-naturally occurring step of modulating the level of differentiation of hemangioblasts to blood vessel cells in the subject. The target tissue may be any tissue in which it is desired to modulate angiogenesis (e.g., ocular, cardiac, limb, or central nervous system tissue).

The level of differentiation of hemangioblasts to blood vessel cells in the subject may be modulated by a number of methods. In one such method, the number of hemangioblasts in the subject is increased or decreased. The number of hemangioblasts in the target tissue of the subject may be increased by any suitable method, including transplantation of hemangioblasts removed from a donor animal into the subject. The donor can be the subject itself or another animal. In one example of such a method, BM cells are first removed from a donor. Hemangioblasts isolated from the population of BM cells are then cultured in vitro under conditions that allow expansion (e.g., proliferation) of the hemangioblasts. Such conditions generally involve growth of the cells in basal medium containing one or more growth factors (e.g., VEGF, SDF-1). Methods of expanding stem cells in vitro are described in T. Asahara Science 275:964-967, 1997. The expanded cells are then administered to the subject. Several approaches may be used for the reintroduction of hemangioblasts into the subject, including catheter-mediated delivery I.V., or direct injection into the heart, brain, or eye. Techniques for the isolation of donor stem cells and transplantation of such isolated cells are known in the art. Autologous as well as allogeneic cell transplantation may be used according to the invention. Alternatively, the number of hemangioblasts in the target tissue of the subject may be increased by administering factors such as VEGF and GM-CSF that increase circulating levels of blood vessel progenitor cells to promote vessel formation. Molecules such as TNF and NO inhibitors may be used in compositions and methods of the invention to decrease hemangioblast self-renewal, and thereby increase differentiation of hemangioblasts into blood vessel cells.

The number of hemangioblasts in the target tissue of the subject may also be decreased by a number of techniques, including administering to the subject an antibody that specifically binds hemangioblasts. Additionally, the number of hemangioblasts in the target tissue of the subject may be decreased by blocking or decreasing recruitment of hemangioblasts from the BM to a non-BM compartment (e.g., target tissue). This may be accomplished by administering to the subject an agent that decreases or prevents recruitment of hemangioblasts from the BM including antibody that specifically binds SDF-1, heparin derivatives (Presta et al., Curr. Pharm. Des. 9:553-566, 2003), inhibitors that target VEGF and its receptors (e.g., anti-VEGF monoclonal antibody, Jain R K, Semin. Oncol. 29(6 suppl. 16):3-9, 2002), and other integrin, selectin, or adhesion molecules that play a role in hemangioblast or leukocyte migration.

In another method of modulating differentiation of hemangioblasts to blood vessel cells, the recruitment or movement of hemangioblasts from the BM to a non-BM compartment (e.g., target tissue) is increased or decreased. A number of substances are known to increase or decrease recruitment of hemangioblasts. Depending on the particular application, any of these might be used in the invention. To increase recruitment of hemangioblasts from the BM to a non-BM compartment (e.g., the target tissue), the administration of any agent capable of promoting recruitment of hemangioblasts may be used. A number of such agents are known. See, e.g., those described in International Application WO 00/50048; SDF-1 alpha, SDF-1 alpha receptor, integrins (e.g., α4, α5), selectin family of adhesion molecules, and colony stimulating factors such as G-CSF. Additionally, the modulation of endogenous factors that increase hemangioblast recruitment may be useful in promoting hemangioblast recruitment from the BM to a non-BM compartment (e.g., target tissue). For example, SDF-1 alpha is a ligand for CXCR4 and has been shown to induce endothelial cell chemotaxis and to stimulate angiogenesis. Thus, to increase recruitment of hemangioblasts from the BM to a non-BM compartment (e.g., target tissue), SDF-1 levels and/or activity can be increased.

Conversely, reducing or blocking SDF-1 activity can be used in a method of decreasing recruitment of hemangioblasts from BM to a non-BM compartment (e.g., target tissue). The level of SDF-1 activity in the subject may be modulated by decreasing the number of SDF-1 molecules available for binding to a SDF-1 binding molecule (e.g., SDF-1 receptor), for example. An antibody that specifically binds to a SDF-1 polypeptide can be administered to the subject to decrease the number of SDF-1 molecules (e.g., polypeptides) available for binding to the SDF-1 receptor, resulting in the prevention or reduction of recruitment of hemangioblasts from BM to a non-BM compartment (e.g., target tissue). In one example of blocking retinal angiogenesis, an antibody that specifically binds SDF-1 is administered to the eye of a subject. The blocking of hemangioblast recruitment from the BM to a non-BM compartment (e.g., target tissue) can also be achieved by administering to the subject other agents that decrease or block migration of hemangioblasts from BM as described above. For example, an antibody against integrins (e.g., α4, α5), selectin family of adhesion molecules, or colony stimulating factors such as G-CSF can be employed.

In methods of increasing the differentiation of hemangioblasts to blood vessel cells, a number of approaches may be employed. For example, alone or in conjunction with hemangioblast transplantation, an agent that is a positive regulator of hemangioblast differentiation (e.g., cytokines, growth factors) may be upregulated or administered to the subject. For example, cytokines that are negative regulators of hemangioblast self-renewal such as TNF (see e.g., Dybedal et al. Blood 98: 1782-91 (2001)) may be administered to the subject to promote differentiation of hemangioblasts. In particular, chemokines, a large family of inflammatory cytokines, have been shown to play a critical role in the regulation of angiogenesis. A number of angiogenesis assays are commonly utilized to screen the angiogenic or anti-angiogenic activity of chemokines. These include in vitro endothelial cell activation assays and ex vivo or in vivo models of neovascularization. The effect of chemokines on endothelium can be assessed by performing in vitro assays on purified endothelial cell populations or by in vivo assays (Bernardini et al., J. Immunol. Methods 273:83-101, 2003). Regulation of angiogenesis by cytokines is reviewed in Naldini et al., Cur. Pharm. Dis. 9:511-519, 2003.

Molecules such as interleukins, interferons, matrix metalloproteinases, and angiopoietin proteins may also be used as agents for modulating (e.g., increasing) angiogenesis in a subject. Nitrous Oxide (NO) is a key regulator of hemangioblast activity. Accordingly, pharmaceuticals such as sildenafil, amino guanidine, L-name, L-nil and AMT that affect NO levels or inhibit the genes that produce NO can also modulate hemangioblast activity by either blocking/promoting recruitment or altering the size and branch structure of the newly formed vessel.

Growth factors such as fibroblast growth factor (FGF), GM-CSF and transforming growth factor β (TGFβ), and VEGF are also useful for promoting differentiation of hemangioblasts and promoting angiogenesis. Such growth factors act by increasing circulating levels of endothelial progenitor cells to promote new blood vessel formation. A review of growth factors and their receptors in proliferation of microvascular endothelial cells maybe found in Suhardja and Hoffman Microsc. Res. Tech. 60:70-75, 2003. Erythropoietin (epo), another pro-angiogenic molecule, has been shown to act synergistically with several growth factors (SCF, GM-CSF, IL-3, and IGF-1) to cause maturation and proliferation of erythroid progenitor cells (Fisher J W, Exp. Biol. Med. 228:1-14, 2003). In a preferred embodiment of increasing angiogenesis, VEGF is administered to the subject to increase differentiation of hemangioblasts and angiogenesis. The VEGF family of growth factors are glycoproteins that are endothelial cell-specific mitogens. VEGF has been shown to stimulate proliferation of endothelial cells and to accelerate the rate at which endothelial cells regenerate. The role of VEGF in angiogenesis is reviewed in Goodgell D S, Oncologist 7:569-570, 2002.

The delivery of a molecule that modulates angiogenesis (e.g., VEGF) can be accomplished using a number of recombinant DNA and gene therapy technologies, including viral vectors. Preferred viral vectors exhibit low toxicity to the host and produce therapeutic quantities of a molecule that modulates angiogenesis. Viral vector methods and protocols are reviewed in Kay et al., Nature Medicine 7:33-40, 2001. Viral vectors useful in the invention include those derived from Adeno-Associated Virus (AAV). A preferred AAV vector comprises a pair of AAV inverted terminal repeats which flank at least one cassette containing a promoter which directs expression operably linked to a nucleic acid encoding a molecule that modulates angiogenesis. Methods for use of recombinant AAV vectors are discussed, for example, in Tal, J., J. Biomed. Sci. 7:279-291, 2000 and Monahan and Samulski, Gene Therapy 7:24-30, 2000.

Useful promoters can be inducible or constitutively active and include, but are not limited to: the SV40 early promoter region (Bernoist et al., Nature 290:304, 1981); the promoter contained in the 3' long terminal repeat of Rous sarcoma virus (Yamamoto et al., Cell 22:787-797, 1988); the herpes thymidine kinase promoter (Wagner et al., Proc. Natl. Acad. Sci. USA 78:1441, 1981); or the regulatory sequences of the metallothionein gene (Brinster et al., Nature 296:39, 1988).

Several nonviral methods for introducing a nucleic acid encoding a molecule that modulates angiogenesis are also useful in the invention. Techniques employing plasmid DNA for the introduction of a nucleic acid encoding a molecule that modulates angiogenesis (e.g., VEGF) are generally known in the art and are described in references such as Ilan, Y. Curr. Opin. Mol. Ther. 1:116-120, 1999; and Wolff, J A. Neuromuscular Disord. 7:314-318, 1997. Methods involving physical techniques for the introduction of a molecule that modulates angiogenesis into a host cell can be adapted for use in the invention. Such methods include particle bombardment and cell electropermeabilization. Synthetic gene transfer molecules that form multicellular aggregates with plasmid DNA are also useful. Such molecules include polymeric DNA-binding cations (Guy et al., Mol. Biotechnol. 3:237-248, 1995), cationic amphiphiles (lipopolyamines and cationic lipids, Felgner et al., Ann. NY Acad. Sci. 772:126-139, 1995), and cationic liposomes (Fominaya et al., J. Gene Med. 2:455-464, 2000).

In a preferred method of adminisistering an agent that is a positive regulator of hemangioblast differentiation, a nucleic acid encoding a VEGF polypeptide contained within an AAV vector is administered to the subject. The AAV vector may be contained within an AAV particle.

To decrease the level of differentiation of hemangioblasts to blood vessel cells, an agent that is a negative regulator of hemangioblast differentiation may be administered to the subject. Any agent that decreases or blocks differentiation of hemangioblasts to blood vessel cells may be used. Such agents include cytokines, transcription factors such as PU.1, hoxB4 and wnt-5A, or VEGF-receptor agonists. The delivery of cytotoxic antibodies that specifically bind and kill hemangioblasts can be used to block differentiation. Alternatively, cytokines that negatively regulate differentiation may be delivered to the host. Specific immunoglobulin therapy can be used to block molecules such as SDF-1 or CXCR-4 (SDF-1 receptor), α4 and α5 integrins, or the selectin family of adhesion molecules thus preventing recruitment of hemangioblasts to sites of retinal ischemic injury, for example. Additionally, hemangioblast recruitment regimens such as administration of G-CSF can be used to alter hemangioblast activity.

Examples of additional molecules that inhibit or mitigate angiogenesis include dopamine agonists and glucocorticoids (Goth et al., Microsc. Res. Tech. 60:98-106, 2003), endostatin (Ramchandran et al., Crit. Rev. Eukaryot. Gene Expression 12:175-191, 2002), sulfonamides and sulfonylated derivatives (Casini et al., Curr. Cancer Drug Targets 2:55-75, 2002), active site inhibitors of urokinase plasminogen activator (Mazar A P, Anticancer Drugs 12:387-400, 2001), chemokines (Bernardini et al., J. Immunol. Methods 273:83-101, 2003), and somatostatin analogues (Garcia de la Torre et al., Clin. Endocrinol. 57:425-441, 2002), and steroids such as triamcinolone. Additionally, agents that inhibit the expression and/or activity of VEGF and VEGF receptors are useful for modulating (e.g., decreasing) angiogenesis in a subject (Sepp-Lorenzino and Thomas, Expert Opin. Investig. Drugs 11:1447-1465, 2002). A review of agents that inhibit angiogenesis at the endothelial cell level is found in Jekunen and Kairemo, Microsc. Res. Tech. 60:85-97, 2003.

The delivery and activity of agents for modulating angiogenesis can be enhanced using any of a number of techniques that target delivery to the vasculature as well as compositions with which to manipulate angiogenesis. For example, a nucleic acid encoding an agent for modulating, such as VEGF or SDF-1, can be linked to an endothelial-specific gene for targeting of the agent to the vasculature. A number of drugs are known that promote aniogenesis, and may be useful in compositions of the invention. For a review of recent advances in angiogenesis and vascular targeting, see Bikfalvi and Bicknell, Trends Pharmacol. Sci. 23:576-582, 2002. The administration and/or recruitment of mast cells, which have been shown to promote angiogenesis (Hiromatsu and Toda, Microsc. Res. Tech. 60:64-69, 2003), may be useful in increasing angiogenesis in a subject.

Isolating Hemangioblasts from Bone Marrow

The invention provides a method for isolating an hemangioblast from the BM of an adult animal. This method includes the steps of isolating bone marrow from the animal, the bone marrow including at least one hemangioblast and at least one non-hemangioblast cell; separating the at least one hemangioblast and the at least one non-hemangioblast cell; and collecting the at least one hemangioblast. Hemangioblasts can be separated from non-hemangioblast cells by any suitable method. In one example of such a method, the BM is contacted with an immobilized agent that specifically binds hemangioblasts but not non-hemangioblast cells. Alternatively, the BM can be contacted with an immobilized agent that specifically binds non-hemangioblast cells but not hemangioblasts. In one variation of these methods, the agent that specifically binds hemangioblasts or non-hemangioblast cells is an antibody.

Uses for Modulating Angiogenesis

Many applications exist for which methods and compositions of modulating angiogenesis would be useful. Compositions and methods of the invention for increasing angiogenesis in a subject may be useful for treating any vasculature-related disorder in which the absence of vasculature causes or is involved in the pathology of the disorder. Examples of such disorders include anemia, ischemia (e.g., limb ischemia, cardiac and brain ischemia), coronary artery disease, and diabetic circulatory deficiencies.

Examples of physiologic states that would also benefit from angiogenesis provided by compositions and methods of the invention include organ and tissue regeneration, wound healing, and bone healing. Angiogenesis is critical to wound repair (Li et al., Microsc. Res. Tech. 60:107-114, 2003). Newly formed blood vessels participate in provisional granulation tissue formation and provide nutrition and oxygen to growing tissues. In addition, inflammatory cells require the interaction with and transmigration through the endothelial basement membrane to enter the site of injury. Among the most potent angiogenic cytokines in wound angiogenesis are VEGF, angiopoietin, FGF, and TGF-β. Administration of such cytokines in conjunction with administration of hemangioblasts of the invention, therefore, would be useful in promoting wound repair.

Increasing angiogenesis using compositions and methods of the invention is useful for treating ischemic conditions. The ability to develop collateral vessels represents an important response to vascular occlusive diseases (e.g., ischemia). Compositions involving hemangioblasts and angiogenic growth factors may be useful for treating subjects with critical limb ischemia as well as myocardial ischemia. Despite continued advances in the prevention and treatment of coronary artery disease (e.g., myocardial ischemia), there remains a population of patients who are not candidates for the conventional revascularization techniques of balloon angioplasty and stenting, or coronary artery bypass grafting. Angiogenesis of ischemic cardiac tissue or skeletal muscle using compositions and methods of the invention may be used to achieve therapeutic angiogenesis in these and other patients. Recent studies have established the feasibility of using angiogenic growth factors such as VEGF and FGF to enhance angiogenesis in patients with limb or myocardial ischemia (Silvestre and Levy, Vale et al., J. Interv. Cardiol. 14:511-528, 2001).

Compositions and methods of decreasing angiogenesis according to the invention can also serve as an effective therapy for such disorders as diabetic retinopathy. Diabetic retinopathy is a major public health problem and it remains the leading cause of blindness in people between 20 and 65 years of age. Like other blinding diseases, diabetic retinopathy is related to an aberrant angiogenic response (reviewed in Garnder et al., Surv. Ophthalmol. 47 (suppl. 2):S253-262, 2002; and Spranger and Pfeiffer, Exp. Clin. Endocrinol. Diabetes 109 (suppl. 2):S438-450, 2001). In one example of a method of treating diabetic retinopathy, antibodies specific to SDF-1 alpha are administered to a patient, resulting in prevention of angiogenesis.

Additionally, compositions and methods of the invention may be useful for treating and preventing cancerous tumor growth by restricting blood supply. Uncontrolled endothelial cell proliferation is observed in tumor neovascularization and in angioproliferative diseases. Cancerous tumors cannot grow beyond a limited mass unless a new blood supply is provided. Control of the neovascularization process, therefore, represents a therapeutic modality for malignant tumors. Solid-tumor cancers that may be treated using compositions and methods of the invention include gliomas, colorectal carcinomas, ovarian and prostate cancer tumors.

Mammalian Subjects, Target Tissues, Target Cells and Stem Cells

The invention provides compositions and methods involving modulating angiogenesis of a target tissue in a subject by modulating differentiation of hemangioblasts to blood vessel cells and modulating hemangioblast recruitment to a target tissue of a subject (e.g. mammalian). Mammalian subjects include any mammal such as human beings, rats, mice, cats, dogs, goats, sheep, horses, monkeys, apes, rabbits, cattle, etc. The mammalian subject can be in any stage of development including adults, young animals, and neonates. Mammalian subjects also include those in a fetal stage of development. Target tissues can be any within the mammalian subject such as retina, liver, kidney, heart, lungs, components of gastrointestinal tract, pancreas, gall bladder, urinary bladder, the central nervous system including the brain, skin, bones, etc.

Transplanting Isolated Hemangioblasts and BM into a Subject

The cells, compositions and methods of the invention can be used to generate as well as regenerate vasculature in a subject (e.g., humans) by cell transplantation. To generate or regenerate vasculature in a subject, cells may be transplanted into a subject by any suitable delivery method. In one method, cells are isolated from a donor animal. Hemangioblasts are isolated from the BM cells and then introduced into the subject. Several approaches may be used for the introducing of hemangioblasts into a subject, including catheter-mediated delivery of I.V., or direct injection into a target tissue, e.g., heart, brain or eye.

Hemangioblasts isolated from BM can be administered to a subject (e.g., a human subject suffering from vascular damage) by conventional techniques. For example, hemangioblasts may be administered directly to a target site (e.g., a limb, myocardium, brain) by, for example, injection (of cells in a suitable carrier or diluent such as a buffered salt solution) or surgical delivery to an internal or external target site (e.g., a limb or ventricle of the brain), or by catheter to a site accessible by a blood vessel. For exact placement, the cells may be precisely delivered into brain sites by using stereotactic injection techniques.

The cells described above are preferably administered to a subject (e.g., mammal) in an effective amount, that is, an amount effective capable of producing a desirable result in a treated subject (e.g., modulating angiogenesis in a subject). Such therapeutically effective amounts can be determined empirically. Although the range may vary considerably, a therapeutically effective amount is expected to be in the range of 500-$10^6$ cells per kg body weight of the animal.

SDF-1 Alpha-Specific Antibodies

The invention relates to modulating the level of SDF-1 activity in a subject by administering to the subject an antibody that specifically binds to a SDF-1 polypeptide. SDF-1 alpha proteins and/or SDF-1 alpha protein receptors such as CXCR4 (or immunogenic fragments or analogs thereof) can be used to raise antibodies useful in the invention according to well known techniques. Such proteins can be produced by recombinant techniques known in the art.

In addition to modulating the level of SDF-1 activity in a subject, antibodies useful in the invention can also be used, for example, in the detection of a SDF-1 alpha protein (or SDF-1 alpha protein receptor) in a biological sample, e.g., a retina section or cell. Antibodies also can be used in a screening assay to measure the effect of a candidate compound on expression or localization of SDF-1 alpha protein or SDF-1 alpha protein receptor. Additionally, such antibodies can be used to interfere with the interaction of a SDF-1 alpha protein and other molecules that bind the SDF-1 alpha protein such as a SDF-1 alpha protein receptor.

Administration of Compositions

The compositions described above may be administered to animals including rodents and human beings in any suitable formulation. Compositions of the invention may be administered to the subject neat or in pharmaceutically acceptable carriers (e.g., physiological saline) in a manner selected on the basis of mode and route of administration and standard pharmaceutical practice. Compositions for modulating angiogenesis may be formulated in pharmaceutically acceptable carriers or diluents such as physiological saline or a buffered salt solution. A description of exemplary pharmaceutically acceptable carriers and diluents, as well as pharmaceutical formulations, can be found in Remington's Pharmaceutical Sciences, a standard text in this field, and in USP/NF. Other substances may be added to the compositions to stabilize and/or preserve the compositions.

Administering Viral Vectors to a Subject

Viral vectors can be used in a method for modulating angiogenesis in a subject. In this method, a viral vector (e.g., AAV) having a nucleic acid encoding VEGF is administered to an animal in a manner in which the nucleic acid becomes expressed. Administration of viral vectors (e.g., AAV) to an animal can be achieved by direct introduction into the animal, e.g., by intravenous injection, intraperitoneal injection, or in situ injection into target tissue. For example, a conventional syringe and needle can be used to inject a viral vector particle suspension into an animal. Depending on the desired route of administration, injection can be in situ (i.e., to a particular tissue or location on a tissue), intramuscular, intravenous, intraperitoneal, or by another parenteral route.

Parenteral administration of vectors or vector particles by injection can be performed, for example, by bolus injection or continuous infusion. Formulations for injection may be presented in unit dosage form, for example, in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the vectors or vector particles may be in powder form (e.g., lyophilized) for constitution with a suitable vehicle, for example, sterile pyrogen-free water, before use.

Effective Doses

The compositions described above are preferably administered to a mammal (e.g., rodent, human) in an effective amount, that is, an amount capable of producing a desirable result in a treated subject (e.g., modulating angiogenesis in the subject). Toxicity and therapeutic efficacy of the compositions utilized in methods of the invention can be determined by standard pharmaceutical procedures. As is well known in the medical and veterinary arts, dosage for any one animal depends on many factors, including the subject's size, body surface area, age, the particular composition to be administered, time and route of administration, general health, and other drugs being administered concurrently.

EXAMPLES

Example 1

Materials and Methods

Generation of gfp chimeric mice: The gfp transgenic mouse strain used as the donor strain was obtained from The Jackson Laboratory (Bar Harbor, Me.). The strain carries gfp driven by chicken beta-actin promoter and CMV immediate early enhancer. All cell types within this animal express gfp. C57B6.gfp radiation chimeric mice (n=46) were generated by irradiating recipient C57BL6 mice with 950 rads followed by intravenous injection of either whole BM ($1 \times 10^6$) or purified hemangioblasts ($2 \times 10^5$) from gfp$^+$ donor mice. Hemangioblasts were purified from adult BM as follows: harvested marrow was made into a single cell suspension and plated onto treated plastic dishes in IMDM+20% FBS for 4 hrs. Non-adherent cells were collected and three rounds of lineage antibody depletion (B220, CD3, CD4, CD8, CD11b, Gr-1, TER 119) were performed with the Miltyni magentic activated cell sorting (MACS) system until a small aliquot stained with PE-conjugated Lineage Ab cocktail showed >95% lineage negative by FACS. The Lin$^-$ cells were then positively selected for Sca-1 for 2-3 rounds until an aliquot showed greater then 95% Sca-1$^+$, Lin$^-$ purity had been achieved. The Sca-1$^+$, Lin$^-$ cells were then stained for CD45 to confirm hematopoietic origin. For the serial transplants approximately 1,000 re-purified hemangioblasts were transplanted. For single hemangioblast transplants Sca-1+, c-kit+, Lin– hemangioblasts were enriched by FACS sorting prior to individual hemangioblast selection with micromanipulators via fluorescent microscopy. Individual Gfp+ hemangioblasts were then mixed with $2 \times 10^5$ non-Gfp+ BM cells that had been depleted of Sca-1+ cells by magnetic beads prior to transplant into irradiated hosts.

Induction of retinal neovascularization: After durable hematopoietic reconstitution was established, chimeric mice were injected i.o. with AAV-VEGF followed at one month with i.p. 10% sodium fluorescein. Fifteen minutes later, they underwent laser treatment. An Argon Green laser system (HGM Corporation, Salt Lake City, Utah) was used for retinal vessel photocoagulation with the aid of a 78-diopter lens. The blue-green argon laser (wavelength 488-514 nm) was applied to selected venous sites next to the optic nerve. Venous occlusion was accomplished using laser parameters of 1-sec duration, 50 μm spot size, and 50-100 mW intensity.

Data collection and analysis: Three weeks after laser treatment, mice were killed and their eyes enucleated. Technical limitations prevented the use of flat-mounted retinas for both confocal microscopy and for immunocytochemistry. The thickness of the retina (approximately 200 microns) prevented adequate penetration of antibody. Therefore, selected mice (n=10) were perfused with buffer containing Hoechst stain in order to label nuclei and delineate the vascular lumen. Eyes (n=20) from treated radiation chimeras were sectioned and stained with hematoxylin. Sections were counter-stained with PE-conjugated anti-Factor VIII or Biotin-conjugated anti-PECAM-1 and anti-MECA-32 followed by avidin-PE (BD BioSciences, San Jose, Calif.) to identify endothelial cells. A minimum of 30 sections per eye was examined for the presence of gfp$^+$, PE$^+$ cells.

This methodology prevented the visualization of intact capillary tufts detectable by confocal microscopy of whole flat-mounted retina. For confocal visualization mice (n=36) were perfused with 3-5 mL of 50 mg/mL tetramethyl rhodamine isothiocyanate (TRITC)-conjugated dextran (160,000 avg. MW, Sigma Chemical Co., St. Louis, Mo.) in phosphate-buffered formaldehyde, pH 7.4, administered through the left ventricle. Immediately afterwards, the eyes were removed and the retinas dissected and mounted flat for confocal microscopy using Vectashield mounting medium (Vector Laboratories, Burlingame, Calif.) to inhibit photo-bleaching. The Olympus IX-70, with inverted stage, attached to the Bio-Rad Confocal 1024 ES system was used for fluorescence microscopy. A Krypton-Argon laser with emission detector wavelengths of 598 nm and 522 nm was used to differentiate the red and green fluorescence. The lenses used on this system were the (Olympus) 10X/0.4 Uplan Apo, 20X/0.4 LC Plan Apo, 40X/0.85 Uplan Apo, 60X/1.40 oil Plan Apo and 100X/1.35 oil Uplan Apo. The software was OS/2 Laser Sharp. Peripheral blood and BM was also collected for donor contribution analysis by FACS with lineage specific antibodies conjugated to PE (BD BioSciences, San Jose, Calif.).

Example 2

Transplanted Animals Exhibit Functional Hemangioblast Activity

Irradiated C57BL6 recipients were transplanted with either whole BM, or highly enriched hemangioblasts, or single hemangioblast from ubiquitous gfp mouse donors to generate radiation chimeras that are designated as C57BL6.gfp. A FACS analysis of purified hemangioblasts and multilineage reconstitution was performed. Transplanted cells were deemed to be highly enriched for hemangioblasts as a result of 1) selection by differential adherence (MSC adhere to tissue culture plastic, hemangioblasts do not), and 2) further selection of non-adherent cells by Ficoll centrifugation followed by purification for Sca-1$^+$ Lin$^-$ phenotype. Single gfp$^+$ hemangioblasts were initially purified as a Sca-1$^+$, c-kit$^+$, Lin$^-$ population by FACS followed by individual selection with micromanipulators via fluorescent microscopy prior to transplant. In these chimeras, marrow- or hemangioblast-derived cells express gfp were identified visually as green cells. A combination of site-specific growth factor over-expression and ischemic insult was used to elicit retinal neovascularization in these C57BL6.gfp chimeras. Initial studies attempted to use either laser occlusion or local expression of VEGF, but either treatment alone failed to-result in consistent neovascularization. In contrast, the combination of site-specific VEGF expression followed by laser-induced venous occlusion resulted in increased numbers of preretinal vessels and consistent preretinal neovascularization.

Initially, primary hemangioblast transplant recipients were monitored for durable, multilineage hematopoietic reconstitution prior to ischemic induction. Six months post hemangioblast transplant and one month after injury, the eyes from treated radiation chimeras were sectioned and stained with hematoxylin. Animals were perfused with buffer containing Hoechst stain in order to label nuclei and delineate the vascular lumen. Induction of a pre-retinal neovascularization was observed in a mouse eye that underwent intravitreal injection with recombinant AAV containing the VEGF gene followed by laser-induced venous occlusion. A gfp+, hemangioblast-derived green endothelial cell has integrated into the lumen of a vessel. The sections were counter-stained with either PE-conjugated anti-Factor VIII, or anti-PECAM-1 and anti-MECA-32 conjugated to biotin with a PE-avidin secondary to confirm the endothelial nature of the green cell. It was clearly observed that the gfp+ cells that surround the lumens (outlined by Hoechst staining) also react with the red fluorescent Factor VIII or PECAM-1 antibodies to produce yellow cells in the combined images, thus, confirming that they are endothelial cells of donor origin. Examination of a minimum of 30 sections per retina, sampling on both sides of the optic nerve, demonstrated that every gfp+ cell found surrounding a lumen reacted with an endothelial cell specific antibody. The pattern of vascular development induced in the model was readily seen in flat mounts of retina perfused with red fluorescent-labeled dextran. In fluorescence micrographs, the patterns of vascular development in C57B6.gfp chimeric mice that underwent intravitreal injection with AAV followed by laser-induced venous occlusion were detected. A representative flat mount of the entire retina of an injured ischemic eye showed areas with newly regenerated blood vessels that have endothelial cells derived from donor gfp+ hemangioblasts. The non-injured eye of the same animal showed gfp+ cells circulating through intact vessels with no apparent contribution to endothelial cells of the vessels. In injured eyes, cells expressing gfp were seen throughout the retinal vasculature, including within capillary tufts that represent new vascular growth. Numerous areas of newly formed capillary tubes expressing gfp were observed that stretch across areas of preexisting vasculature. Merged green and red channels visualized the yellow tubes of newly formed blood vessels because gfp+ endothelial cells have produced lumens capable of being perfused with rhodamine. Importantly, all five mice transplanted with highly enriched hemangioblasts (~95% Sca-1+, Lin−) contained numerous new vessels composed of gfp+ cells, which were easily visualized in all quadrants of the retina. A minimum of two new areas of neovascularization were observed in every field examined, indicating most injuries were repaired, in part, with donor derived cells. In contrast, mice (n=10) receiving whole BM exhibited a decreased frequency of gfp+ cells in areas of neovascularization. This indicates that the greater the number of hemangioblasts transplanted to generate the chimera the greater the number of donor-derived endothelial cells that can be visualized. All transplanted animals, however, exhibited functional hemangioblast activity, as defined by repopulation of the blood and regeneration of blood vessels that co-enriches with the hemangioblast.

The classic definitive assay for HSC function in murine models is durable long-term reconstitution of the hematopoietic system in irradiated hosts. Subsequent transplantation of secondary lethally irradiated hosts with enriched BM hemangioblasts from primary transplants demonstrated the ability of HSC to expand and self-renew, thus satisfying the definition of a stem cell. Serial transplantation tends to preclude MSC participation in the reconstitution because there is no evidence to indicate that MSC are able to serially engraft. To confirm that the production of "green" endothelial cells observed during neovascularization was a property of the self-renewing long-term repopulating HSC, secondary transplants of highly purified HSC derived from primary recipients were performed. For primary recipients, five animals were lethally irradiated and transplanted with highly purified gfp+ HSC. Animals were monitored for 10 months to ensure durable, multilineage hematopoietic reconstitution. Gfp+ HSC were then purified from the primary recipients and transplanted into five secondary hosts for induction of hemangioblast activity. Following confirmation of multilineage hematopoietic reconstitution in the secondary recipients after three months, these animals were scored for hemangioblast activity derived from gfp+ HSC. Retinal ischemia was induced and resultant neovascularization was analyzed at four months post secondary transplant. The vascular lumens from a treated retina perfused with rhodamine indicated that gfp+ endothelial cells have participated in the regeneration of induced capillaries. The combined image shows that donor HSC-derived endothelial cells regenerated the entire vascular tuft in the secondary transplant recipient. Thus, a serially transplantable, multiple hematopoietic lineage reconstituting adult HSC (i.e., hemangioblast) clearly has hemangioblast properties and can regenerate functional vasculature.

In order to determine if a single HSC clone could make both blood and blood vessels, the model was repeated with animals that were reconstituted with a single HSC. Following FACS sorting, individual Gfp+, Sca-1+, c-kit+, Lin− HSC were manually isolated and transplanted along with 2×10$^5$ Sca-1 depleted non-Gfp marrow. The depleted marrow served as a source of short-term hematopoietic progenitors to enhance single HSC engraftment. The single HSC provided multilineage hematopoietic reconstitution and robust endothelial cell contributions to new vessel formation. This new vessel formation was observed in all three animals undergoing single HSC transplantation and provides definitive proof that a single adult HSC can function as a hemangioblast.

Example 3

Inhibition of Retinal Neovascularization

The hemangioblast model described above in Examples 1 and 2 was used to test the effect of anti-SDF-1 antibody on retinal neovascularization. In the present example, the hemangioblast model featuring a particular modification was used. Specifically, the eyes of the mice were injected with antibody that blocked SDF-1 activity. This experiment showed that retinal neovascularization was blocked by neutralizing SDF-1 activity (e.g., intravitreal injection of anti-SDF-1 antibodies). Treatment of the eye completely blocked gfp+ hemangioblast-derived neovascularization of ischemic retinas. Fluorescence confocal micrographs showed blocking of hemangioblast-driven neovascularization by anti-SDF-1 antibody. Normal incorporation of gfp+ hemangioblast derived cells into new blood vessels in the rodent eye was observed. The blocking of SDF-1 activity in the eye prevented the incorporation of Gfp+ hemangioblasts into blood vessels. An example of a protocol for blocking Gfp+ hemangioblast-derived neovascularization of ischemic retinas is detailed below.

First, GFP males were euthanized by cervical dislocation under general anesthesia and BM from the males was harvested. Cells stained for c-kit APC and sca-1 PE were FACS sorted. While cells were sorting, BL6 females were lethally irradiated (850 RADS). Next, a BM transplantation was performed by retinal orbital sinus (ROS) injections with the sorted cells on the irradiated BL6 mice. Three weeks after the ROS injections, tail bleeds were performed. The FACS Caliber was used to check for engrafment of the sca-1/c-kit cells. Next, recombinant AAV (rAAV)-VEGF was injected intravitreally into the right eye of the positively engrafted mice. Four weeks after the VEGF injections, retinal laser photocoagulation was performed in the right eye. Immediately following the lasering procedure, monoclonal anti-SDF-1 antibody (R&D Systems MAB310) was injected intravitreally in the right eye. PBS was intravitreally injected into the untreated eye. Intravitreal injection of anti-SDF-1 antibody was performed once every week for the following four weeks. Animals were then anesthetized and perfused by cardiac puncture (left ventricle) with 3 ml TRITC-Dextran in 4% buffered formaldehyde. The retinas from both treated and untreated eyes were subsequently dissected. The retinas were mounted flat in buffered glycerin and imaged by confocal microscopy.

Using additional cohorts of animals, the experiment described above was repeated. Animals were treated with either SDF-1 antibody or mock-treated with PBS via intravitreous injections, and then retinal ischemia was induced in the animals. The animals were perfused with red dye to show vessels and imaged by confocal microscopy. The SDF-1 antibody injections completely blocked gfp+ hemangioblast derived green blood vessel formation while the mock injected animals formed green gfp+ hemangioblast derived blood vessels as expected in response to retinal ischemia. Fluorescence confocal micrographs of multiple mice transplanted with either gfp+ hemangioblasts or mock-injected with PBS showed vessels that formed subsequent to induction of ischemia. Gfp+ hemangioblast derived green blood vessels showed normal function. Confocal imaging showed that new blood vessel formation in animals that received intravitreous injection of anti-SDF-1 antibody did not occur.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of decreasing angiogenesis in a mammalian eye comprising injecting into a mammalian eye a composition comprising an anti-SDF-1 antibody wherein injection of the composition comprising the anti-SDF-1 antibody decreases neovascularization of the mammalian eye retina by adult hemangioblasts, and examining the eye for an absence of blood vessels comprising cells differentiated from adult hemangioblast cells.

2. The method of claim 1, wherein injecting the mammalian eye with the composition comprising the anti-SDF-1 antibody decreases the number of adult hemangioblasts in the retina.

3. The method of claim 1, wherein injecting the mammalian eye with the anti-SDF-1 antibody decreases recruitment of adult hemangioblasts from bone marrow to the retina.

4. The method of claim 1, wherein the retina has been subjected to hypoxic insult prior to injecting into the mammalian eye the composition comprising the anti-SDF-1 antibody.

5. A method of treating diabetic retinopathy comprising injecting into a mammalian eye a composition comprising an anti-SDF-1 antibody, wherein injection of the composition comprising the anti-SDF-1 antibody decreases neovascularization of the mammalian eye retina by adult hemangioblasts, and examining the eye for an absence of blood vessels comprising cells differentiated from adult hemangioblast cells.

6. The method of claim 1, wherein the anti-SDF-1 antibodies are MAB310 antibodies.

* * * * *